United States Patent [19]
Schob

[11] Patent Number: 5,868,994
[45] Date of Patent: Feb. 9, 1999

[54] CONSTANT CURRENT NEEDLE ANNEALING

[75] Inventor: George Schob, Princeton Junction, N.J.

[73] Assignee: Ethicon, Inc., Somerville, N.J.

[21] Appl. No.: 659,492

[22] Filed: Jun. 6, 1996

[51] Int. Cl.⁶ .................................................. C21D 1/06
[52] U.S. Cl. ............................ 266/252; 219/50; 219/282
[58] Field of Search .................................... 266/249, 252; 219/50, 282, 290

[56] References Cited

U.S. PATENT DOCUMENTS

| | | | |
|---|---|---|---|
| 2,957,123 | 10/1960 | Rose ........................................ | 219/282 |
| 3,746,582 | 7/1973 | Gentry . | |
| 3,842,239 | 10/1974 | Ellinghausen et al. . | |
| 3,962,898 | 6/1976 | Tillmann . | |
| 4,063,065 | 12/1977 | Wust ........................................ | 219/50 |
| 4,115,685 | 9/1978 | Grandin et al. ........................... | 219/50 |
| 4,295,033 | 10/1981 | Lindgren et al. . | |
| 4,409,042 | 10/1983 | Dornberger et al. . | |
| 5,477,604 | 12/1995 | Smith et al. . | |

FOREIGN PATENT DOCUMENTS

| | | |
|---|---|---|
| 25 33 288 | 2/1977 | Germany . |
| 128919 | 12/1977 | Germany . |
| 29 49 819 A1 | 9/1980 | Germany . |
| 29 49 842 A1 | 9/1980 | Germany . |
| 33 26 162 A1 | 2/1985 | Germany . |
| 48-43762 | 12/1973 | Japan . |
| 2 091 002 A | 7/1982 | United Kingdom . |

*Primary Examiner*—Scott Kastler
*Attorney, Agent, or Firm*—Scully, Scott, Murphy & Presser

[57] ABSTRACT

A constant current annealing device for annealing a wire or surgical needle is disclosed. The device includes amplitude and time setting devices, such as thumb-wheel switches. A constant current source is connected to the current setting device. The constant current source is switchable, through a switch for example, in response to a timing signal to provide a constant current for a predetermined duration. A pair of spaced apart electrodes are clamped on the needle and a switching device is connected between the constant current source and the pair of electrodes. The voltage drop across the switching device varies to compensate for load variations, thus keeping the anneal current constant in the anneal ON mode. In the anneal OFF mode, where current is not provided to the needle, the switching device shunts a residual current away from the electrodes. The time setting device include a programmable logic controller (PLC) and a solid state relay to provide an accurate timing signal. A current measuring and monitoring device is connected to another PLC, which shuts down the annealing device after a predetermine number of alarms or after the constant current amplitude deviates by a predetermined amount.

13 Claims, 6 Drawing Sheets

CONSTANT CURRENT NEEDLE ANNEALING

BACKGROUND OF THE INVENTION

1. Field of the Invention

The present invention is directed to a device and method for the continuous high speed and high current electric resistance heating and annealing of wires, and more particularly, to a constant current surgical needle annealing device and method.

2. Discussion of the Prior Art

Surgical needles are formed from wires cut to provide needle blanks. After processing one end of the needle blank to a desired needle shape, excess portion of the needle blank is cut. Prior to cutting the excess needle blank, the portion to be cut is annealed or heated. This softens the portion to be cut to facilitate cutting and further processing, such as forming a channel or drilling a hole in the soft portion for suture insertion.

Annealing may be performed using flames, conventional ovens, induction heating or resistance heating. U.S. Pat. No. 4,295,033 (Lindgren) discloses an annealing oven. Conventional annealers suffer from a number of disadvantages, such as limited accuracy, consistency and speed. Some flame annealers are limited to rack or manual operations. Open flames, including a pilot light, increase the danger of accidents, oxidize the needle, and deposit carbon and soot on the needle. Further, heat sinks may be required to confine the anneal zone. Heat transfer from flame annealing is inconsistent due to variations in flame temperature, gas pressure, and flame application time or traverse rate. Moreover, there is no feedback or indication of proper or improper annealing. In addition, the speed of annealing is low, thus reducing the overall needle manufacturing output.

Various types of flame annealers have been used to anneal a specific portion of a wire or needle blanks. Flame annealers may be used in a continuous needle forming process where needle blanks are mounted on a carrier strip 15, as shown in FIG. 1. Alternatively, flame annealers are used with a batch needle forming process. In batch needle forming processes, needles are formed in batches. A batch of needle blanks are manually arranged on a fixture or rack for processing. The fixture may be an integral part of the annealing mechanism. Alternatively, the fixture may have its own free standing mechanism which is attached to the annealing mechanism.

A motor may control exact positioning of the rack mounted needle blanks. The rack mounted needle blanks may be presented to various operations requiring organized presentation of needle blanks or needles. Such operations include grinding, channel forming, curving, needle blank cut-off, drilling, annealing, needle point forming, needle body forming, needle passivation, de-greasing, electro-polishing, washing, rinsing, drying, and coating with a lubricating substance, such as silicon mixture for example.

Annealing a portion of the needle blank prior to cut-off may be performed by introducing a flame and moving either the flame or the rack in a controlled fashion. One type of flame annealers, referred to as a channel flame annealer, uses a long fixed continuous burner tube. Fuel for the flame may be natural or bottled gas (propane or butane) mixed with air or compressed air. The burner tube may be a standard pipe or tubing with series or rows of drilled holes to provide flames. Wider holes provide a wider flame to anneal a wider portion of the needle blanks.

A timer controls duration of the flame, turning the flame on and off, or controls duration of the needles blanks in a continuous flame. This controls the heat transfer to the needle blank portion or anneal zone. A heat sink is used to confine the anneal zone. The duration of the flame may be controlled by electrically controlling a gas solenoid, which when opened, uses a pilot light or a piezo crystal to ignite the entire burner.

Alternatively, the duration of the needle blanks in the combustion zone may be controlled by moving the rack in and out of the combustion zone using conventional mechanical means. For example, a pivoting fixture receiving mechanism is used to lower the fixture mounted needle blanks into a position of engagement with the combustion zone. The duration of the engagement may be pre-set using a conventional timing mechanism. The timer setting may be realized by mechanical means, such as engagement of rotational means which applies a rotational action to the pivoting fixture receiving mechanism. The timer mechanism, through an air actuation means, could also allow the pivotal motion of the fixture receiving mechanism to be transferred through a cylinder means. This provides the proper duration of the needle blanks engagement with the combustion zone.

This channel flame annealer may be semi-automatic, where a micro-switch detects presence of the rack, actuates cylinders which clamp and locate the rack having needle blanks thereon, and automatically starts, times, and stops the anneal cycle.

In another flame annealer, referred to as a precision flame annealer, the burner itself is moved in and out of anneal zones of a batch or individual needle blanks mounted on the rack. The duration of annealing is controlled by a conventional timing mechanism. The burner may be a single small port burner or a multi-port long burner. The small burner may traverse the rack mounted needle blanks to heat one needle at a time in a very precise zone. Heat transfer is controlled by the speed of traverse. The burner may be moved by conventional means, such as a linear motor, a motor driven ball screw or timing screw, a motor with rack and pinon, or an air cylinder. This precision flame annealing may be semi-automatic, where loading the rack activates the anneal cycle.

In higher speed annealing, propane or similar fuels mixed with air may not burn hot enough. Instead, oxygen or other flammable gases, e.g., hydrogen, may be mixed with conventional fuels or methane, to achieve a more consistent and higher burning temperature. Despite increased speed, flame annealers are still slow and typically limited to 20 parts per minute.

Instead of mounting the needle blanks on a fixture or rack, the needle blanks may be mounted on the carrier strip 15 shown in FIG. 1. This increases annealing speed and needle production output. For a stationary flame, the strip mounted needle blanks may be continuously moved or indexed, pausing for a brief moment withing the flame. The limiting factor is again consistency and repeatability of the heat transfer. Using intense heat, anneal timing is critical for proper annealing. Due to the high intensity heat, even a slightly long anneal time leads to burning or melting the anneal zone portion of the needle blanks. Precise regulation of gas pressure or flame temperature is needed. This is difficult to achieve and still may not lead to a repeatable annealing. To improve annealing, a hydrogen gas generator is used and a small amount of alcohol is added as a flash suppressant.

The conventional flame annealers suffer from low speed. To increase annealing speed, laser flame annealers have been used. Laser high speed flame annealers provide a hot flame at a fairly precise anneal zone without the need for heat sinks. However, such annealers require a complex fuel supply and have some drift in the heat output. Other disadvantages include lack of feedback, presence of open flames, and difficulty in achieving repeatability.

Resistance annealers heat the anneal zone by passing a current therethrough. Current is passed through a pair of spaced electrodes clamped at two ends of the anneal zone. This current heats the wire potion 25 (FIG. 1) located between the clamped electrodes to the annealing temperature. Delivered heat to the anneal zone portion of the wire equals the product of time and the square of the current as shown in equation (1):

$$H = I^2 T \qquad (1)$$

where: H is total heat;

I is current; and

T is time or duration.

Conventional resistance annealers do not suffer from some of the flame annealer disadvantages. For example, soot or carbon build-up is eliminated. The annealer has dual clamping contacts which are cam operated. The anneal cycle is cam actuated. However, conventional resistance annealers operate at low speed, such as 10 parts per minute, and are limited to use with small wire sizes. This is because conventional resistance annealers have a maximum current of approximately 20 amps. In addition, no feedback is provided and proper annealing is manually checked, e.g., by viewing the color of the annealed wire. Color of the annealed portion ranges from gold, red, blue to silver. Determining the properness of annealing by viewing is imprecise and subjective.

In addition, current is monitored using an oscilloscope and adjusted manually with a potentiometer. The current duration is determined using an electromechanical timer having a resolution of 0.1 seconds. Such annealers are inaccurate, slow and require operator intervention. Conventional resistance annealers are complex, cannot operate at high speed, and suffer from inadequate precision and high failure rate of annealed wires or needles.

Other conventional resistance annealers measure voltage or temperature of the annealed wire to adjust the current therethrough. A resistance annealer which measures temperature is disclosed in U.S. Pat. No. 4,409,042 (Dornberger). Such annealers require complex reflectors and are not suitable for high speed annealing. Speed is limited due to the response time of temperature sensors. UK Patent Application GB 2 091 002 (Ash) discloses a wire annealer where wire resistance is measured as a representation of wire temperature. U.S. Pat. No. 3,746,582 (Gentry) also discloses wire annealing, wherein temperatures are controlled by varying the current through the spaced contacts for heating the wire portion located between the contacts. Other resistance annealers are disclosed in U.S. Pat. No. 3,842,239 (Ellinghausen), and U.S. Pat. No. 3,962,898 (Tillmann). These annealers are not suitable for high speed, high precision annealing.

SUMMARY OF THE INVENTION

High speed annealing, e.g., at a rate of 120 parts per minute, requires high precision. At 120 parts per minute, the duration of each total anneal cycle is 0.5 seconds or 500 milli-seconds (msec). This includes indexing the needle blank, clamping the electrodes or contacts thereon, switching the current "on", applying the current for a desired time (timing out), and switching the current "off". The mechanical actions of indexing and contact clamping consume approximately 75% of the available anneal cycle time. This leaves ⅛ second or 0.125 msec for the actual anneal. In this short anneal time, the delivery of heat is critical in that the duration and amplitude of the current must be precisely controlled. Conventional annealing devices cannot deliver repeatable precise current amplitude for a precise duration at high speed. Current amplitude of conventional annealing devices varies due to load or AC power line changes, contact wear, and needle surface contamination.

It is therefore an object of the present invention to provide a constant current annealing device and method that eliminate the problems of conventional resistance annealing.

Another object of the present invention is to provide a resistance annealing device that supplies constant current irrespective of load or AC power line changes, contact wear, or needle surface contamination.

Another object of the present invention is to provide a resistance annealing device that has high current output for large wire annealing.

Another object of the present invention is to provide a resistance annealing device that performs high speed accurate annealing.

Another object of the present invention is to provide a resistance annealing device that has a fast switch response.

Yet another object of the present invention is to provide a resistance annealing device that is safe to operate, having enclosed contacts and no open flames.

A further object of the present invention is to provide a resistance annealing device that allows high precision and repeatability from one anneal cycle to another.

Still a further object of the present invention is to provide a resistance annealing device that alerts operators of an inaccuracy in the annealing current amplitude and automatically stops the annealing after a predetermined number of incorrect current readings, or when the current amplitude changes by a predetermined amount.

These and other objects of the present invention are achieved by a constant current annealing device for annealing a wire or a surgical needle comprising a reference circuit for setting a desired annealing time and current amplitude. The reference circuit includes a current setting device which generates a current amplitude signal, and a time setting device which generates a timing signal. Illustratively, the amplitude and time setting devices are thumb-wheel switches.

A pair of spaced apart electrodes are clamped on the needle. A constant current source is connected to the reference circuit and provides a constant current for annealing the needle. A switching device is connected between the constant current source and the pair of electrodes. The constant current source provides a constant current through the pair of electrodes when the switching device is in one position.

In one embodiment, a voltage drop across the switching device varies in response to changes in a voltage drop across the needle so that the anneal current, flowing through the needle, remains constant. In another embodiment, the switching device shunts a residual current away from the pair of electrodes when the switching device is in another position.

The constant current source is switchable, through a switch for example, in response to a timing signal that represents the set current or anneal time. This provides a constant current for the set anneal duration.

The constant current source comprises a constant voltage generator which generates a constant voltage in response to the set current amplitude. A power supply supplies the constant current, and is connected to a first terminal of a reference resistor. The second terminal of the reference resistor is connected to receive the constant voltage. This provides a constant voltage drop across the reference resistor resulting in the generation of the constant current.

The reference circuit includes a timing programmable logic controller and a solid state relay having high resolution. The timing programmable logic controller controls the solid state relay to generate a timing signal.

A current measuring device connected to one of the electrodes measures an amplitude of the constant current. The current measuring device may be a hall effect transformer placed around a line connected to one of the electrodes. A display, such as a digital display, may be connected to the current measuring device for displaying an indication of the current amplitude.

A system programmable logic controller triggers the timing programmable logic controller to generate the timing signal when the electrodes are clamped on the wire. The system programmable logic controller shuts off the constant current after the measured amplitude deviates by a predetermined amount, or when a number of improper indications exceeds a predetermined number.

In this embodiment of the present invention, a method for annealing a surgical needle using a constant current annealing device comprises the steps of:
(a) setting a constant current amplitude and a current time;
(b) providing a constant current for the set time to the needle through a switching device; and
(c) varying a voltage drop across the switching device in response to a voltage drop change across the needle.

In the other embodiment, step (c) is substituted by switching the switching device to sink a residual current while switching a switch to stop generation of the current.

The constant current providing step comprises the steps of:
connecting one terminal of the reference resistor to a power supply;
generating a reference voltage using a reference voltage generator; and
switching a switch to provide the reference voltage at another terminal of the reference resistor using an operational amplifier. Another step includes generating a current timing signal using a timing programmable logic controller.
Other steps may include:
setting a current amplitude using a current amplitude setting device;
setting the current time using a current duration setting device;
clamping a pair of spaced apart electrodes on the wire or needle;
generating an anneal signal from a system programmable logic controller indicating a completion of the clamping;
measuring an amplitude of the constant current using a current detector;
indicating a level of the detected current amplitude on a monitoring device; and
stopping the annealing device when the indicated current level exceeds a predetermined level, or when a number of improper indications exceeds a predetermined number.

BRIEF DESCRIPTION OF THE DRAWINGS

Further features and advantages of the invention will become more readily apparent from a consideration of the following detailed description set forth with reference to the accompanying drawings, which specify and show preferred embodiments of the invention, wherein like elements are designated by identical references throughout the drawings; and in which.

DETAILED DESCRIPTION OF THE INVENTION

Surgical needles and methods of manufacturing surgical needles are well known in the art. Surgical needles are formed from wires cut to provide needle blanks which are disposed on a carrier strip for transportation to various stations of a continuous needle forming device. Such a needle forming device is disclosed in U.S. Pat. No. 5,477, 604, entitled "Process for Manufacturing Taper Point Surgical Needles", which issued on Dec. 26, 1995, is assigned to the assignee of the present application and contains subject matter related to the subject matter of the present patent application. The specification of U.S. Pat. No. 5,477, 604 is incorporated herein by reference thereto.

Figure 1:
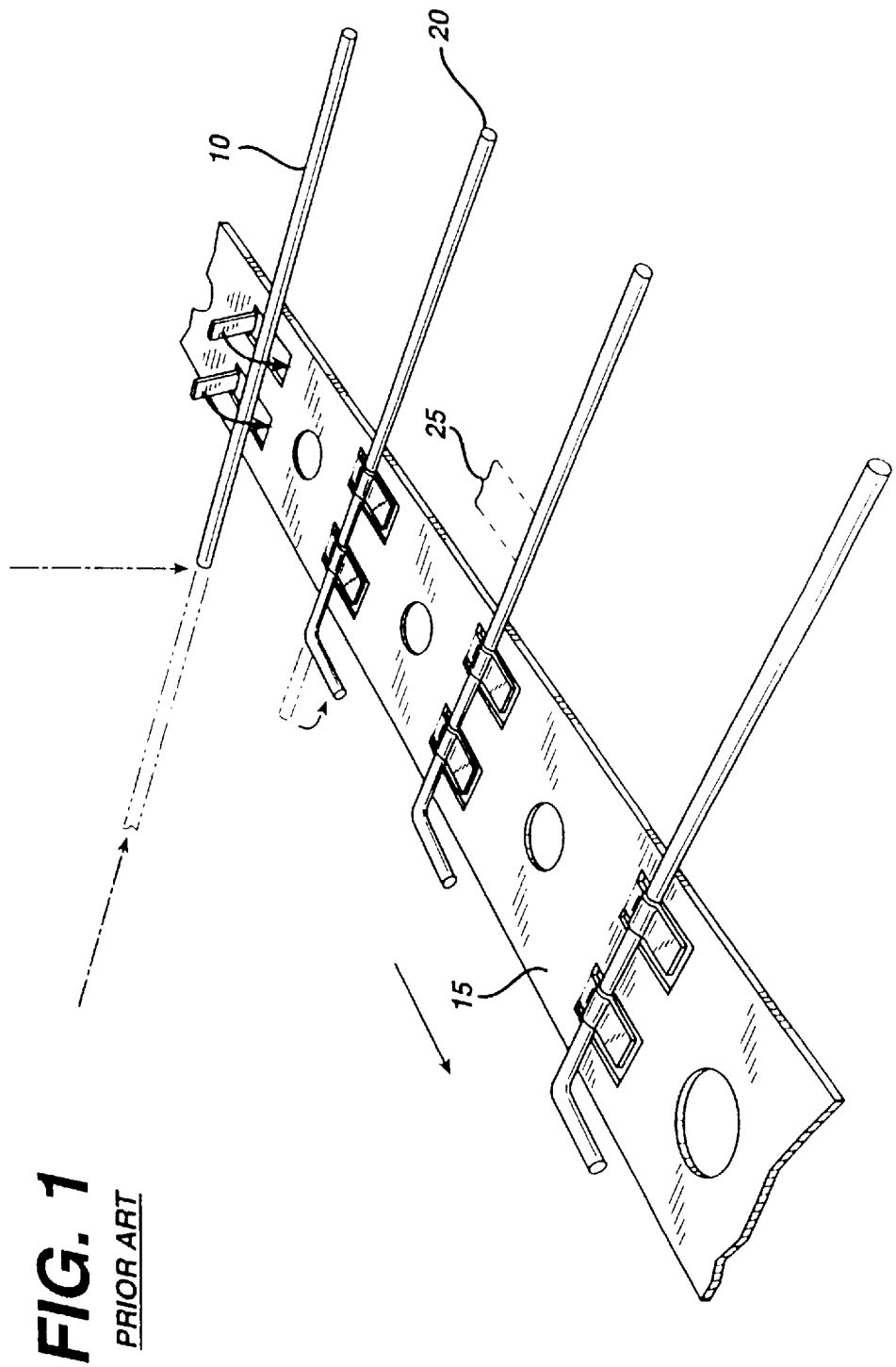
FIG. 1 shows a perspective view of a needle blank mounted on a section of a conventional carrier strip as known in the prior art.

FIG. 1 shows a needle blank 10 mounted on a carrier 15. The needle blanks 10 are processed, e.g., heat treated to strengthen and harden the needle blanks, and a distal end 20 sharpened and shaped into a desired curvature. Processing the needle blanks 10 include annealing proximal portions 25 of the needle blanks 10 to soften the portion 25 prior to cutting.

Annealing the portion 25 heats it to a temperature close to but below a transformation temperature. The portion 25 is then slowly cooled. This is often referred to as partial annealing. Partial annealing the portion 25, softens the metal located at the portion 25 to a point that preserves some of the added strength and hardness from prior heat treatments.

Annealing duration and temperature of the needle blank portion 25 prior to cutting must be accurately controlled to achieve a desired softness of the wire portion 25. Deviating from the desired annealing temperature and time results in the portion 25 being too soft or too hard. Inappropriate strength of the potion 25 causes failures during subsequent manufacturing steps or during use.

Figure 2A:
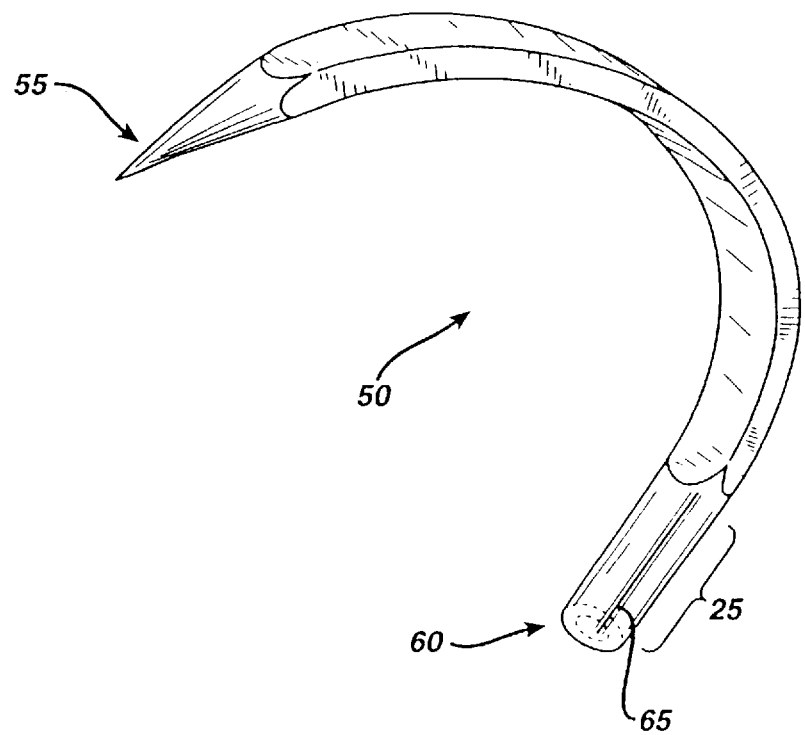
FIG. 2a shows a perspective view of a conventional needle having a channel as known in the prior art.
Figure 2B:
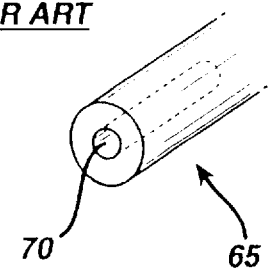
FIG. 2b shows a perspective view of a drilled distal end of a conventional needle as known in the prior art.

FIG. 2a shows a surgical needle 50 having a sharp distal end 55. The proximal end 60 is the portion 25 which had been annealed prior to cutting the needle blank 10 shown in FIG. 1. A channel 65 is cut into the distal end 60. A suture is placed in the channel 65 and held in place by crimping the channel 65. Instead of the channel 65, a hole may be drilled into the distal end 60. FIG. 2b shows a distal end 60 having a hole 70 therein.

Surgical sutures may be attached or mounted to the proximal ends 60 in various ways. One common way is to have the channel 65 formed into the proximal end of the needle 50 as shown in FIG. 2a. The channel end typically is die-formed into a needle 50 during the manufacturing process and consists of a cavity. When a surgical suture end or tip is placed into the cavity 65, the channel end 60 is hit with a die one or more times under pressure forcing the channel sidewalls to close tightly about the suture tip. This prevents suture separation from the needle. The process of mounting a suture tip to the proximal end 60 of a needle 50 is known in the art as swaging.

As shown in FIG. 2b, another manner in which a suture may be mounted to a surgical needle is by drilling a hole 70, referred to in the art as a blind hole, into the proximal end 60 of the needle 50. This can be done using conventional mechanical drilling devices or conventional laser drilling devices. The end or tip of a suture is then inserted into the drilled hole 70, and the section of the proximal end of the needle surrounding the blind hole 70 is swaged in a conventional manner by compressing with various conventional dies.

Improper and inconsistent annealing of the proximal end 60 causes various problems. If the annealing occurs for too long or delivers excessive heat to the portion 25 to be annealed, then the portion 25 becomes excessively soft. A suture may not be properly held in the channel 65 or hole 70 of the proximal end 60 after swaging. The suture may separate from the needle, or the needle may bend during subsequent processing, handling or use.

If the annealing does not deliver enough heat to properly soften the proximal end 60, then the hard or brittle proximal end 60 may crack during swaging. In addition, the hard proximal end 60 quickly wears out cutting edges of tools, such as cut-off dies, drill bits, and swaging tools. This requires frequent tool replacement and is costly. Cost increases not only due to the cost of cutting tool replacement, but also due to reduced needle output, for example, resulting from interruption of a continuous manufacturing process.

The need for consistent annealing is even more apparent for needles produced in batches, rather than in a continuous manufacturing process, where destructive tensile strength testing is performed on a representative needle from the batch.

It is essential that annealing be precisely controlled. By controlling the annealing temperature, duration and cooling cycle, a wide range of metallurgical properties may be obtained including relative strength, hardness or ductility.

Figure 3:
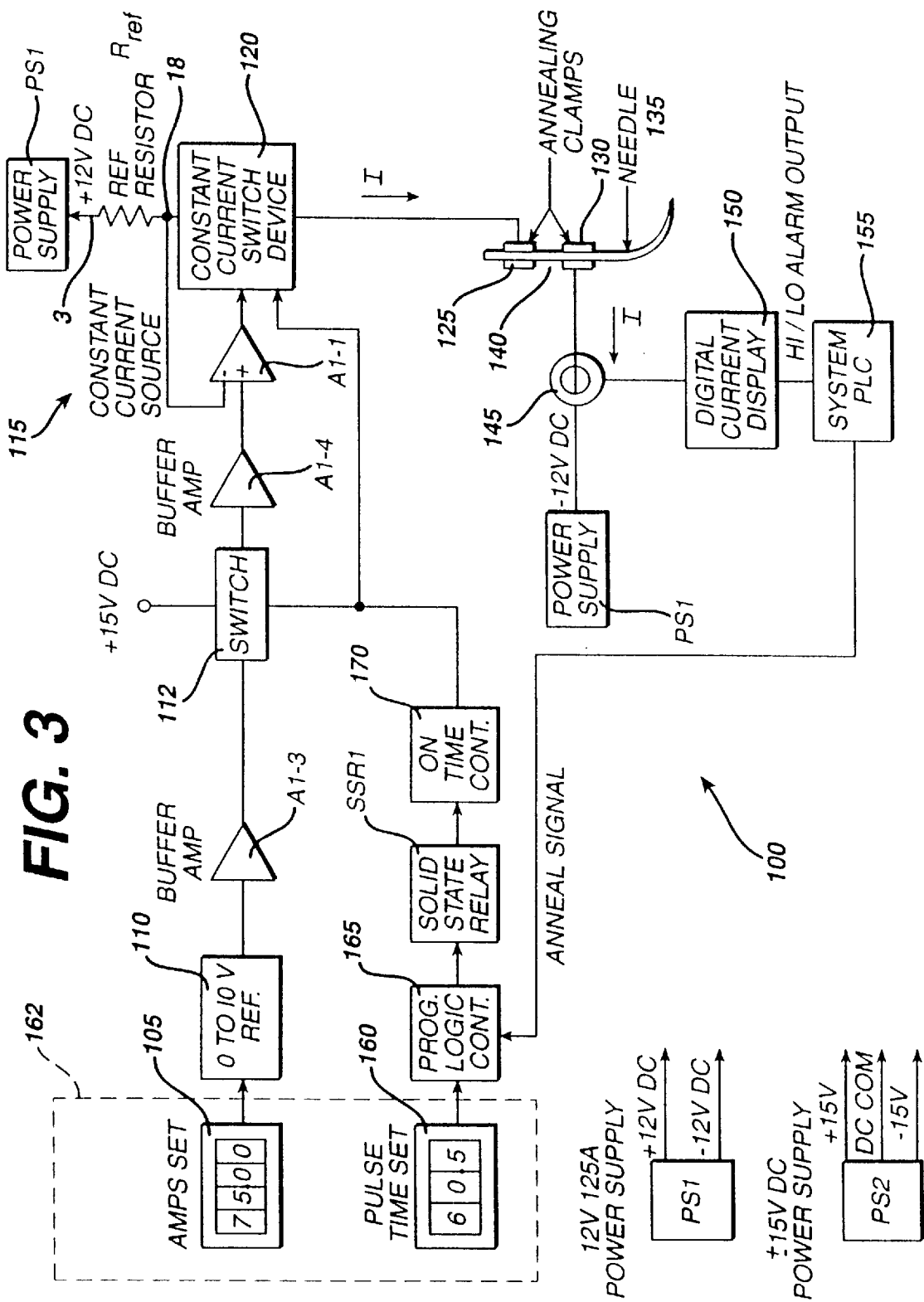
FIG. 3 shows a block diagram of a constant current resistive annealer according to the present invention.

FIG. 3 shows an illustrative block diagram of a constant current resistive annealing device 100 according to the present invention. The device 100 comprises at least one reference circuit 162 for setting the duration and amplitude of the current applied during annealing of a needle 135. As illustrated in FIG. 3, this reference circuit 162 includes two adjustable devices having individual circuits for setting anneal curent time and amplitude. The first adjustable device is for setting the desired annealing current amplitude, referred to as a current amplitdue setting device 105, which may be a thumb-wheel switch. The thumb-wheel switch 105 generates a preset signal for determining the current amplitude applied during the annealing step. This preset signal is supplied to a reference voltage generator 110. Illustratively, the reference voltage generator 110 generates a reference voltage $V_{ref}$ from 0 to 10 volts and is connected to the input of a buffer amplifier A1-3. A potentiometer may be connected between the reference voltage generator 110 and the buffer amplifier A1-3 to adjust the amplitude of the reference voltage $V_{ref}$. The output of the buffer amplifier A1-3 is connected to the input of another buffer amplifier A1-4 through a switch 112. The buffer amplifiers A1-3, A1-4 have high input impedances and low output impedances to provide isolation. This keeps constant the voltage at the output of buffer A1-4 and prevents this constant output voltage from being susceptible to noise. The output of the buffer amplifier A1-4 is connected to the input of a constant current source 115.

The constant current source 115 comprises a constant voltage generator A1-1 which may be an operational amplifier (op amp) having inverting and non-inverting inputs. The non-inverting input of the op amp A1-1 receives an isolated and adjusted DC voltage (derived from the reference voltage $V_{ref}$) from the output of the buffer A1-4. The output of op amp A1-1 is connected to a constant current switching device 120. The inverting input of the op amp A1-1 is connected to one terminal 18 of a reference resistor $R_{ref}$. The voltage levels at both inputs of the op amp A1-1 are equal. Thus, the DC voltage at the non-inverting input of op amp A1-1, (which DC voltage is provided by the reference generator 110 through a potentiemeter, and the buffer amps A1-3, A1-4 and switch 112,) is also provided to the node or terminal 18 through the inverting input of op amp A1-1. This reference voltage at node 18 remains constant regardless of noise or changes in the output voltage of the op amp A1-1.

The other terminal 3 of the reference resistor $R_{ref}$ is connected to a power supply PS1. The power supply PS1 supplies the constant current I used for annealing the needle 135. Illustratively, the power supply PS1 is a +12 vdc, 125 amps power supply, having a resolution of 10 milli-amps.

The switching device 120 is connected to a first contact or electrode 125. The first electrode 125 is spaced from a second electrode 130. Both electrodes 125, 130 are clamped on a wire or needle 135. For safety, the electrodes 125, 130 are enclosed to prevent accidental contact therewith. The second electrode 130 is connected to the return −12 vdc of the power supply PS1. The constant current I passes through a portion 140 of the needle 135 located between the spaced apart electrodes 125, 130.

The current I remains constant despite load/needle resistance changes. This is because the voltage drop across the switching device 120 changes in response to voltage drop changes across the needle portion 140. The voltage drop change across the switching device 120 occurs since the total voltage between the two terminals, (positive and negative terminals,) of the power supply PS1 is a constant 12 vdc, and the voltage drop across the reference resistor $R_{ref}$ is constant, due to the constant voltage $V_{18}$ at node 18.

A current measuring or sensing device 145 is connected to one of the electrodes 125, 130 to measure or detect the amplitude of the constant current I. Illustratively, the current sensing device 145 is a hall effect transformer looped around a line connecting the second electrode 130 to the −12 vdc return of the power supply PS1.

A display 150, such as a digital display, is connected to the current sensing device 145 to provide in-line continuous feedback alarm outputs, which may be audible alarms in addition to visual indicators. The display may indicate the numerical value of the constant current I. Alternatively, or in addition, the digital display may have indications, such as three lamps, that indicate the amplitude of the constant current I as being "high", "low" or "OK". The "high" and "low" alarm signals are also be connected to a system programmable logic controller 155 (PLC).

The system PLC 155 may be programmed in any desired configuration to control automatic shut-off or provide alarm signals. For example, if the value of the detected or measured current deviates from the desired constant current value by a predetermined amount, then the system PLC 155 may shut down the annealing process and stop a portion of the needle manufacturing assembly line. Alternatively, the syatem PLC 155 may be programmed to allow, for example, two consecutive incorrect current readings, and shut down the annealing upon three consecutive incorrect readings of annealing current amplitudes.

The second adjustable device of the reference circuit 162 includes a time setting device 160, which may be another thumb-wheel switch. The time setting device 160 and the current amplitdue setting device 105 form the reference circuit 162 for setting the desired annealing time and amplitude. The timing thumb-wheel 160 is connected to a timing PLC 165, which is connected to the system PLC 155. The timing PLC 165 generates a digital timing signal upon being triggered by an anneal signal from the system PLC 155. The anneal signal indicates that the electrodes 125, 130 are clamped on the wire or needle 135, which is ready for annealing.

The duration or pulse-width of the digital timing signal is a function of the setting of the time thumb-wheel 160. The duration and amplitude of the constant current provide the proper annealing temperature, as discussed in connection with equation (1). Illustratively, the constant current amplitude ranges from zero to 100 amps in 10 milli-amp increments, whereas the duration of the constant current, or pulse width of the timing signal ranges from 1 to 999 milli-seconds (msec), in increments of 1 msec.

The output of the timing PLC 165 is connected to a solid state relay SSR1 to control switching thereof. Illustratively, the solid state relay SSR1 has a resolution of 1 msec. The solid state relay SSR1 outputs a timing signal or pulse having a pulse-width which is similar to the digital timing signal but is more accurate. In addition, the timing signal provided by the solid state relay SSR1 has an amplitude which is different from the amplitude of the digital timing signal from the timing PLC 165. Illustratively, the timing pulse has a zero volt baseline and a +15 volts amplitude. The solid state relay SSR1 is connected to an ON-time controller 170 which supplies the timing pulse to the switch 112 and the switching device 120.

When the timing signal is high, the switch 112 allows the reference voltage generated from the reference voltage generator 110, in response to the setting of amplitude thumb-wheel 105, to reach the non-inverting input of the op amp A1-1. In turn, op amp A1-1 provides a constant voltage to terminal 18 of the reference resistor $R_{ref}$. At the same time, the high timing signal causes the constant current switch 120 to allow current to flow toward the contacts 125, 130 for annealing the needle portion 140. In addition, the constant current switch 120 maintains the annealing current at a constant amplitude.

Since the voltage of the other terminal 3 of the reference resistor $R_{ref}$ is a constant +12 vdc, supplied by the power supply PS1, the voltage drop across the reference resistor $R_{ref}$ is constant. In addition, the voltage drop across the positive and negative terminals of the power supply PS1, (connected to node 3 and the contact 135, respectively,) is a constant 12 vdc. The constant voltage drops across the constant reference resistor $R_{ref}$ and across the two terminals of the power supply PS1, provide a constant anneal current I. The anneal current I remains constant regardless of load variations, such as contact 125, 130 wear, because the voltage drop across the constant current switch 120 changes in response to voltage drop changes across the needle 135 so that the entire voltage drop, between the two terminals of the power supply PS1 remains a constant 12 vdc.

When the timing signal from the on time controller 170 is low, the switch 112 prevents the reference voltage from the reference voltage generator 110 to reach the op amp A1-1. Instead, the switch 112 provides +15 vdc to the op amp A1-1, which holds the voltage and node 18 at +15 vdc. This prevents current flow from the power supply PS1 since the voltage (+15 vdc) at node 18 is larger than the voltage (+12 vdc) at node 3.

At the same time, the low timing signal from the solid state relay SSR1 causes the constant current switch 120 to shunt or sink any residual current away from the contact 125. This provides a fast response time, and quick and clean transition between current/anneal ON and current/anneal OFF states.

Figure 4A:
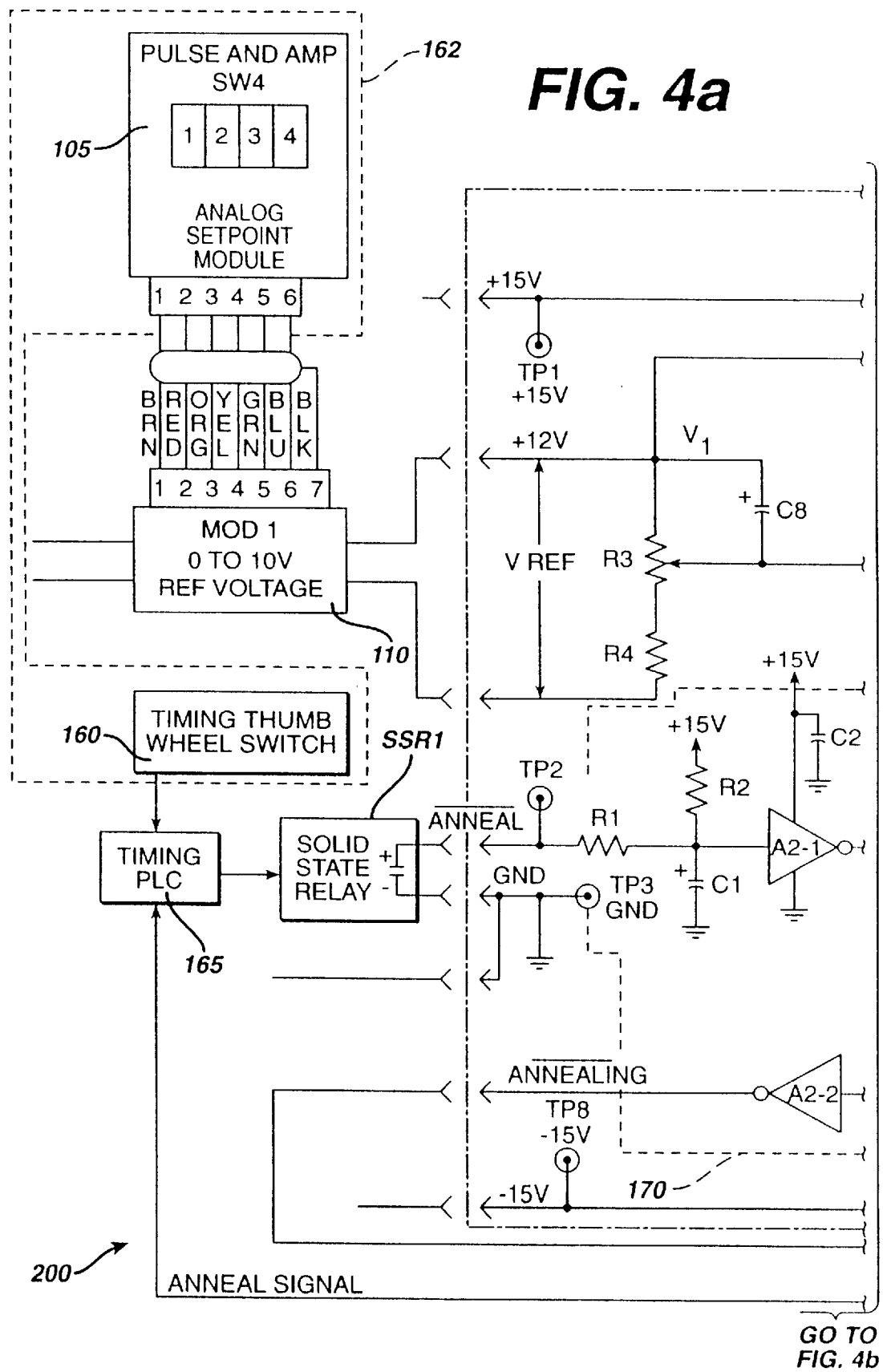
FIGS. 4a 4b and 4c show a schematic of the annealer of FIG. 3 according to the, present invention.
Figure 4B:
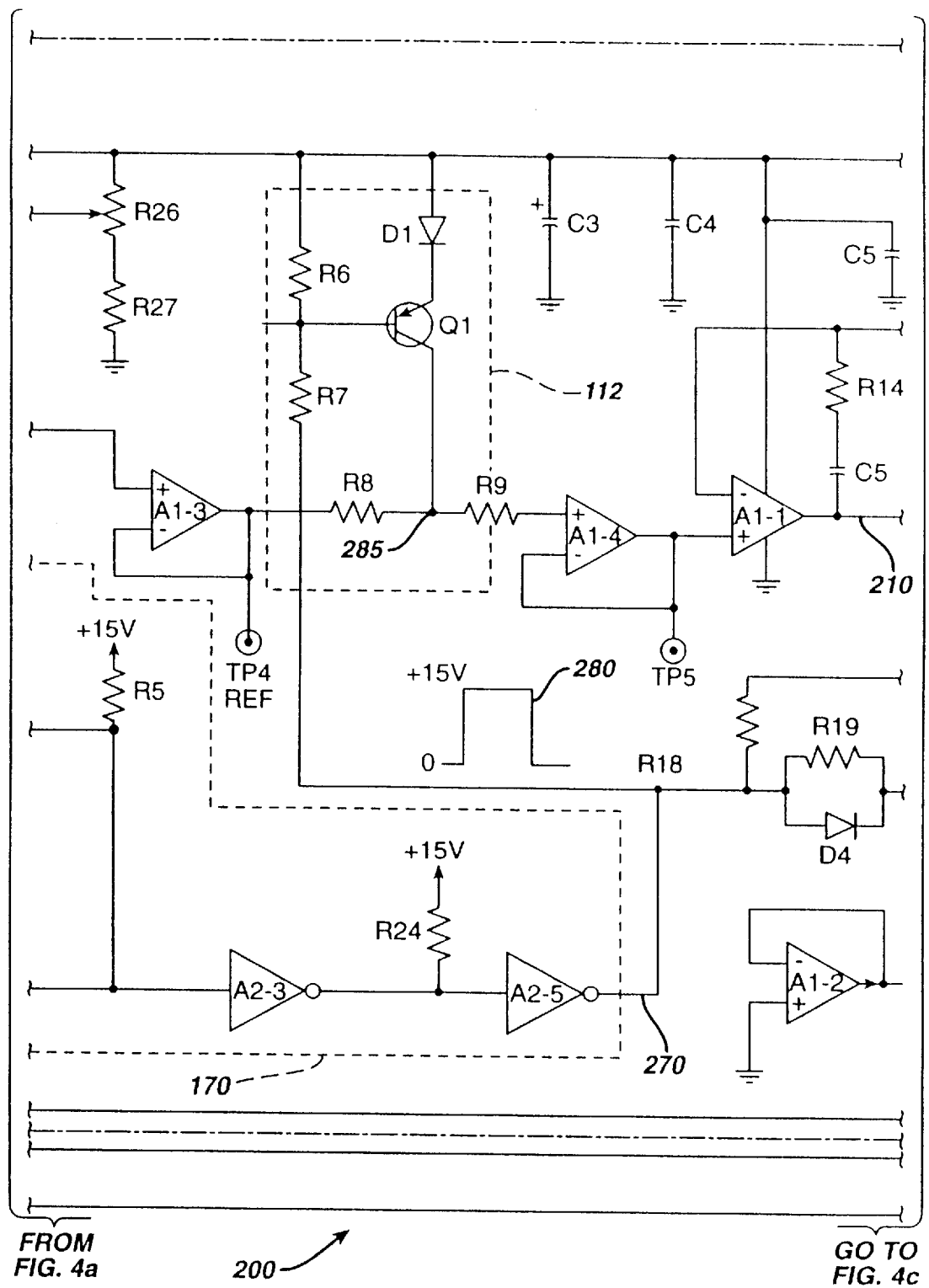
Figure 4C:
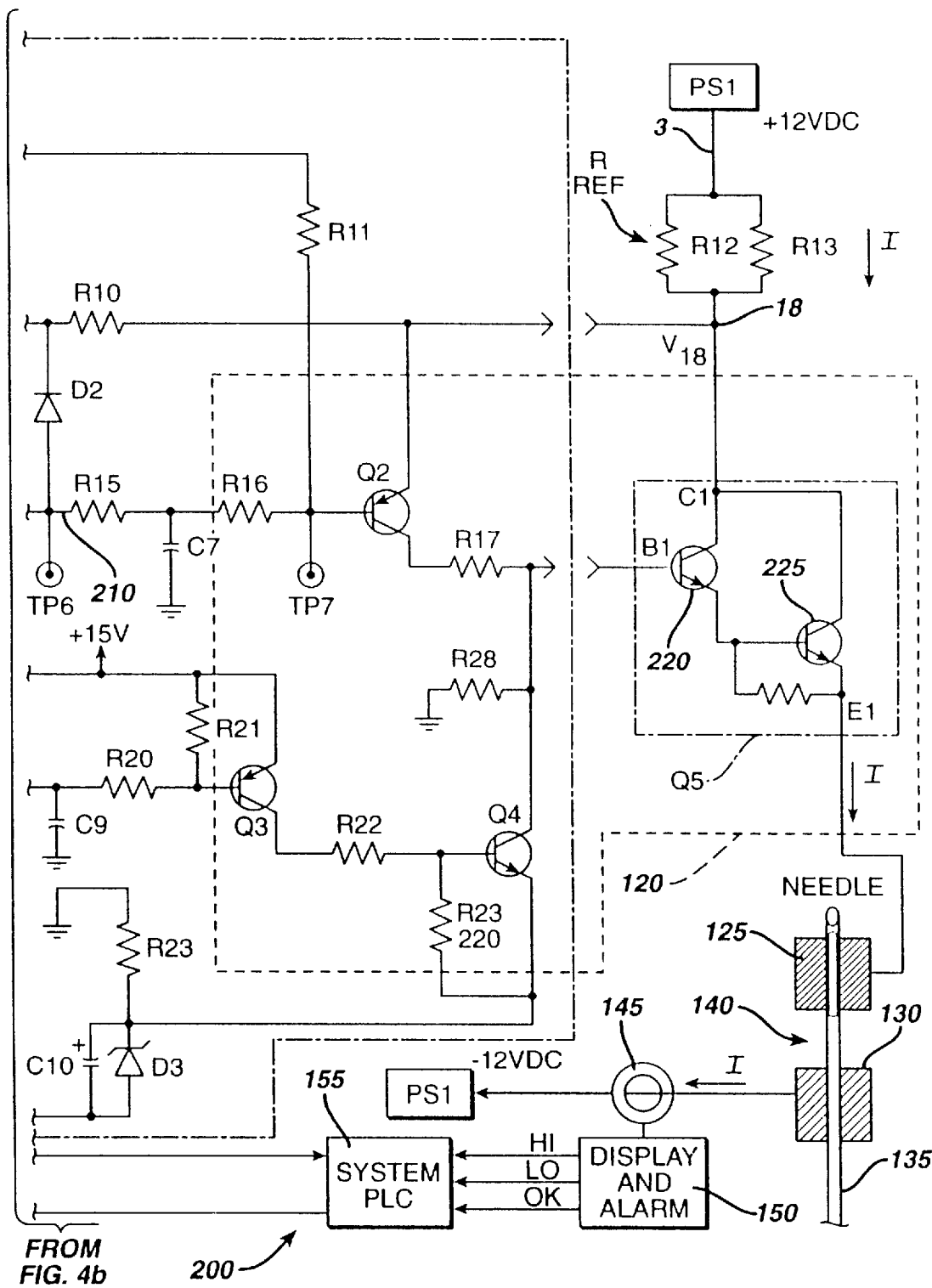

FIGS. 4a–4c shows an illustrative detailed schematic of an electrical circuit 200 which may be used to implement the block diagram reistive annealer 100 of FIG. 3. The electrical circuit 200 provides a precise constant anneal current for a precise duration and comprises a current amplitude thumb-wheel switch 105 which is connected to an input of a 0–10 v reference voltage generator 110. For example, a setting of 00.00 on the amplitude thumb-wheel 105 provides 0 v reference voltage, whereas a setting of 99.99 provides a 10 v reference voltage. The output of the reference voltage generator 110 is connected to a non-inverting input of an operation amplifier (op amp) A1-1 through a first resistive divider, two voltage followers or buffer amps A1-3 and A1-4, and a second resistive divider R8, R9. The first resistive divider includes resistor R4 and potentiometer R3. A second potentiometer R26 having one end connected to the +15 vdc bus, has an armature connected to the first potentiometer R3. The potentiometer R26 provides +12 vdc to one terminal of the potentiometer R3. In turn, the potentiameter R3 provides a reference voltage from 0 to 12 vdc. Various resistors are connected between the reference generator 110 and op amp A1-1 to provide voltage division and proper biasing.

The voltages at the two inputs, i.e., the inverting and non-inverting inputs, of the op amp A1-1 are equal. The output 210 of the op amp A1-1 varies to keep the two A1-1 inputs equal. Thus, in the anneal ON mode, the reference voltage from the potentiameter R3 is also present at the inverting input of op amp A1-1, which inverting input is connected to node 18 to provide a constant collector voltage $V_{18}$. Node 18 is one terminal of the reference resistor $R_{ref}$, and a common collector of npn transistors 220, 225.

The constant collector voltage $V_{18}$ equals the reference voltage from potentiameter R3 and is protected from noise immunity by buffers A1-3, A1-4. In addition, the collector voltage $V_{18}$ remains constant regardless of voltage changes in the output 210 of the op amp A1-1.

A diode D2, connected between the output 210 and inverting input of op amp A1-1, prevents the output 210 from exceeding the inverting input by more than the diode voltage drop, e.g., 0.7 volts. A capacitor C5 and resistor R14 are connected in series between to output 210 and inverting input of op amp A1-1 to provide feedback and stability.

The output 210 of the op amp A1-1 is also connected to the base of a pnp transistor Q2 through biasing resistive dividers R15, R16. Transistor Q2 switches or turns on and off depending on the value of the voltage at output 210. The collector of transistor Q2 is connected to the base B1 of an npn transistor 220 through a small biasing resistor R17, which may have a value of 10 ohms. The emitter of the pnp transistor Q2 is connected to the common collectors of npn transistors 220, 225. In the anneal On mode, transistor Q2 is on and turns on transistor 220, which turns on transistor 225. Transistors 220, 225 are collectively referred to as Q5, and together with transistors Q2, Q3, Q4 (where transistors Q3 and Q4 are discussed below) form part of the constant current switching device 120, shown in FIGS. 3 and 4a–4c.

Two precision reference resistors R12, R13, which are connected in parallel, are also connected to the A1-1 op amp output 210. Illustratively, the two parallel resistors R12, R13 each have a value of 0.1 ohms, to result in a reference resistance $R_{ref}$ having an effective value of 0.05 ohms. The other terminals of the reference resistors R12, R13 are connected to a positive terminal 3 of a +12 vdc, 125 amp power supply PS1. The power supply PS1 provides a constant current I to the needle 135 through the a pair of electrodes 125, 130. The two electrodes 125, 130 are spaced and clamped on the needle 135 in the needle portion 140 to be annealed.

One electrode 125 is connected to an emitter El of the npn transistor 225. The other electrode 130 is connected to the return side of the +12 vdc power supply PS1.

A timing thumb-wheel switch 160 is set by an operator to apply current I through the needle portion 140 for a desired duration. The timing thumb-wheel 160 switch and the current amplitude thumb-wheel 105 switch form the reference circuit 162 for setting the duration and amplitude of the anneal current I. The timing thumb-wheel switch 160 is connected to a solid state relay SSR1 through a time PLC 165. The solid state relay SSR1 is connected through a series of inverters and biasing resistors to the base of a pnp transistor Q3. An output 270 of an inverter is connected to the biasing resistors.

Collector of the pnp transistor Q3 is connected through a resistor to the base of an npn transistor Q4. Emitter of the transistor Q4 is connected to −15 vdc power bus, while the collector of transistor Q4 is connected to the base B1 of npn transistor 220. A second power supply PS2, shown in FIG. 3, provides +15 vdc high a −15 vdc return. The second power supply PS2 also has a dc (direct current) common line. A small resistor R28, e.g., 22 ohms, is connected between the collector of transistor Q4 and ground.

In addition to being connected to the biasing resistors of pnp transistor Q3, the inverter output 270 is also connected to the base of a pnp transistor Q1 through a biasing resistor R7. Another biasing resistor R6 is connected between the base of transistor Q1 and a +15 vdc bus. The emitter of transistor Q1 is also connected to the +15 vdc bus through a diode D1. The collector of pnp transistor Q1 is connected to a non-inverting input of the voltage follower A1-4 through a resistor R9. Various capacitors shunt noise to ground. The transistor Q1 acts as a switch, similar to the switch 112 shown in FIG. 3. In the anneal OFF mode, transistor Q1 is on to provide +15 vdc (from the +15 vdc bus, through the diode D1 and buffer amp A1-4) to the non-inverting input of op amp A1-1. This pulls up the voltage at node 18 of the reference resistor $R_{ref}$ to +15 vdc to prevent anneal current flow from the power supply PS1.

The operation of the device 200 will now be explained. An operator sets the current amplitude thumb-wheel switch 105 to a desired number between 00.00 to 99.00, corresponding to a constant anneal current of 0 to 100 amps delivered from the +12 vdc, 125 amp PS1. The output of the current amplitdue setting thumb-wheel switch 105 causes the 0–10 reference voltage generator 110 to provide a reference voltage, shown as $V_{ref}/2$, to the non-inverting input of buffer A1-3. As will be explained below, this reference voltage applies a constant control voltage $V_{18}$ at node 18 during annealing or the anneal ON state.

The operator also set the timing pulse thumb-wheel switch 160 to provide a timing pulse having a desired duration. Illustratively, the thumb-switches 105, 160 are linear, where changing the setting linearly changes the current amplitude and duration, respectively. The timing PLC 165 is triggered or turned on by the anneal signal from the system PLC 155, indicating the electrodes 125, 130 are clamped, and the wire or needle 135 is ready for annealing. The timing PLC 165 outputs a logic pulse having the desired pulse-width or duration, as chosen by setting the timing thumb-wheel switch 160. The logic timing pulse is provided to switch on and off the solid state relay SSR1. Switching the solid state relay SSR1 provides a timing pulse having the same desired pulse-width as the logic timing pulse, but with high accuracy and resolution, e.g., 0.1 msec resolution. However, the amplitude of the timing pulse is +15 volts, e.g., when the solid state relay SSR1 is switched off, and zero volts (i.e., connected to ground) when the solid state relay SSR1 is switched on.

The timing pulse, shown as reference 280, is present at the output 270 of inverter A2-5, after propagating through inverters A2-1, A2-3, and A2-5 that form the ON-time controller 170 shown in FIGS. 3 and 4a–4c. The timing pulse 280 is provided to the base of transistors Q1 and Q3 through biasing resistors.

ANNEAL ON

The wire or needle portion 140 is annealed by a constant current I flowing therethrough when the timing pulse 280 is high, e.g., +15 volts. The high timing signal 280 allows the constant annealing current I to flow from the +12 vdc high terminal of PS1 to its −12 vdc return terminal through the reference resistor $R_{ref}$, transistor Q5, and needle portion 140. This is accomplished as follows.

Q1 turns off when the timing pulse 280 is high. This allows the reference voltage from the 0–10 volts reference generator 110 to pass through the buffers A1-2, A1-4, and op amp A1-1, so that a constant control voltage $V_{18}$ appears at node 18. Node 18 is the reference resistor $R_{ref}$ terminal which is opposite terminal 3 connected to the +12 vdc power supply PS1 high. Transistor Q2 is also on because the output 210 of op amp A1-1 is below the emitter voltage of $V_{18}$.

The turned on transistor Q2 turns on transistor Q5. Because transistor Q5 is on, current I flows from the high side of the +12 vdc, 125 amp power supply PS1, toward the electrode 125. Current I is constant because the control voltage $V_{18}$ and the power supply PS1voltage are constant. This provides a constant voltage drop across the reference resistor $R_{ref}$, and a constant 12 vdc voltage drop across the two terminals of the power supply PS1. Thus, any voltage changes across the needle 135 are compensated by complementary voltage drop changes across the transistor Q5 in order for the voltage drops across the reference resistor $R_{ref}$, and across the two terminals of the power supply PS1 to remain constant. That is, transistor Q5 compensates for any load variations.

An illustrative example is given below. When the current amplitude thumb-wheel switch 105 is set to provide a constant voltage at node 18 of 11.5 volts, (i.e., $V_{18}$=11.5 vdc), then the current through the 0.05 ohm reference resistor $R_{ref}$, having a voltage drop of 0.5 volts, is 10 amps (I=V/R=0.5 volt/0.05 ohms). This current I remains constant irrelevant of contact wear or variation in needle resistance, since such variations are compensated for by variations in the voltage drop across transistor Q5. Transistor Q5 and op amp A1-1 insure that the annealing current I remains constant despite variations in needle and contact resistances. Having constant voltage drops across the constant resistor $R_{ref}$ and across the two terminal of the power supply PS1, along with transistor Q5, provide the constant current I.

The constant current I flows through the first electrode 125 and the needle anneal portion 140. The constant current I exits from the second electrode 130 and flows back to the return terminal −12 vdc of the power supply PS1. The current I does not flow through the rest of the needle 135 since the power supply PS1 is isolated from the needle 135 or chassis ground. In this current or anneal ON state, the +15 volts of the timing pulse 280 turns off transistors Q3 and Q4.

ANNEAL OFF

The annealing constant current I is removed after the desired anneal time, corresponding to the pulse-width of the timing signal 280. Transistor Q1 turns on when the timing pulse 280 is zero volts. The turned on transistor Q1 provides +15 vdc, through diode D1, to node 285 located between resistors R8 and R9 which connect the output of buffer A1-3 to the input of buffer A1-4. The +15 voltage at node 285 produces approximately +15 vdc at node 18. Because the +15 vdc voltage at node 18 is higher than the voltage at the other terminal of the reference resistor $R_{ref}$, i.e., at node 3 which is connected to the +12 vdc power supply PS1, no current flows from the +12 vdc power supply PS1 toward the reference resitor $R_{ref}$.

When transistor Q1 is on, transistor Q2 is off because the output 210 of op amp A1-1, (which is connected to the base of transistor Q2 through the resistive dividers R15, R16, ) is higher than +12 vdc, which is higher than the transistor Q2 emitter voltage at node 18. The turned off transistor Q2 turns off transistor Q5. This turned off transistor Q5 electrically disconnects the first electrode 125 from the reference resistor $R_{ref}$, further preventing any current flow from the +12 vdc power supply PS1 to the first electrode 125. In the anneal off mode, the voltage levels at the emitters of transistors 220, 225 are zero volts.

In addition, to provide a fast and sharp transition between current ON and OFF states, transistors Q3 and Q4 turn on to shunt or sink any residual current from transistor Q5. The turned on transistor Q4 provides −3 vdc to the base of transistor 220. The −3 vdc is produced by connecting a zener diode D3 between the −15 vdc bus and emitter of transistor Q4. The −3 vdc at the base of transistor 220 and the zero volt level at the emitter of transistor 220 provide a fast and sharp turn off of transistors 220, 225.

The zero volt level of the timing signal 280 turns on transistors Q3, Q4. This current sinking by transistors Q3, Q4 eliminates current overshooting or undershooting spikes during transitions between the ON and OFF states. This allows the constant current resistive anneal device 200 to have a fast switch response. The transistor Q4 is a shunting switch which is turned on by transistor Q3, where transistor Q3 itself is turned on when the timing signal 280 is zero volts.

The resistors R17, R28, which are connected to the collectors of transistors Q2, Q4, respectively, have a low value to provide the fast and sharp transitions between current ON and OFF states. This allows the annealing device to have a fast response time and provides the constant anneal current I during a precise and accurate predetermined time.

In the present invention, a method for annealing a wire portion using a constant current annealing device comprises the steps of:
(a) setting a constant current amplitude and time by the reference circuit 162;
(b) providing the constant current I to the needle 135 through the switching device 120; and
(c) varying a resistance of the switching device 120 in response to resistance changes in the needle 135.

In the other embodiment, step (c) is substituted with switching the switching device 120 to sink a residual current while switching a switch 112 to stop generation of the current I.

The constant current providing step comprises the steps of:

connecting one terminal 3 of the reference resistor $R_{ref}$ to the power supply PS1;

generating a reference voltage using the reference voltage generator 110; and switching the switch 112 to provide the reference voltage at another terminal 18 of the reference resistor $R_{ref}$ using the operational amplifier A1-1. Another step includes generating a current timing signal using the timing programmable logic controller 165.

Other steps include:

mounting a plurality of surgical needles onto a carrier strip 15 (FIG. 1);

moving the mounted needles through the annealing device;

setting a current amplitude using the current amplitude setting device 105;

setting the current time using the current duration setting device 160;

clamping a pair of spaced apart electrodes 125, 130 on the wire or needle 135;

generating an anneal signal from a system programmable logic controller 155 indicating completion of the clamping;

measuring an amplitude of the constant current I using a current detector 145;

indicating a level of the detected current amplitude on a monitoring device 150; and stopping the annealing device when the indicated current level exceed a predetermined level, or when a number of improper indications exceed a predetermined number.

The constant current annealing device may be used in-line or off-line to precisely anneal wire or needle portions at high speed. For example, speeds of 120 to 240 parts per minutes are achieved. A constant current having a precise amplitude and duration quickly heats and anneals the wire portion. The current may have a high amplitude, up to 100 amps for example. Larger currents may be delivered by reconfiguring the amplitude thumb-wheel switch 105 and potentiemeter R3. A power supply having greater than 125 amp capability may also be used instead of the power supply PS1 for larger anneal current capabilities.

The constant current annealing device allows high speed and accurate annealing of small wires as well as large wires that require large currents for proper annealing. The needles may be transported using a stepper motor indexing, where each needle is moved and stopped in position for annealing, and moved again after annealing. The electrodes may be metal, ceramic, or a combination thereof. The electrodes may be clamped on the needle through an air driven cylinder or a motor driven mechanical clamping device. This reduces and quickly dampens vibrations resulting from electrode clamping, to further increase needle output speed.

The constant current annealing device provides high repeatability and has a fast switch response. Identical and precise current (amplitude and duration) is applied to each needle, regardless of contact wear, needle surface contamination or AC power line fluctuations. In addition, the constant current annealing device provides automatic annealing where in-line continuous feedback and alarm outputs automatically indicate improper annealing. The constant current annealing device automatically shuts down when a predetermined improper annealing occurs.

The constant current annealing device is safe since the contacts or electrodes are enclosed and there are no open flames. Absence of flames also prevents soot/carbon build-up on the annealed surface.

While the invention has been particularly shown and described with respect to illustrative and preformed embodiments thereof, it will be understood by those skilled in the art that the foregoing and other changes in form and details may be made therein without departing from the spirit and scope of the invention which should be linked only by the scope of the appended claims.

Having thus described our invention, what I claim as new, and desire to secure by Letters Patent is:

1. A constant current annealing device for annealing a surgical needle, said device comprising:
    at least one reference circuit for setting a desired annealing time and current;
    a pair of electrodes spaced apart and clamped on said needle;
    a constant current source connected to said reference circuit, said constant current source providing a constant current through said pair of electrodes for annealing said needle; and
    a switching device connected between said constant current source and said pair of electrodes, said switching device switching in response to a timing signal from said reference circuit, said switching device providing a voltage drop thereacross which varies in response to changes in a voltage drop across said needle so that said current remains constant.

2. The constant current annealing device of claim 1, wherein said constant current source comprises:
    a constant voltage generator which generates a constant voltage in response to said set current;
    a power supply which supplies said constant current; and
    a reference resistor having a first terminal connected to said power supply, and a second terminal connected to receive said constant voltage.

3. The constant current annealing device of claim 1, wherein said constant current source is switchable through a switch between on and off states in response to said set annealing time.

4. The constant current annealing device of claim 1, wherein said reference circuit comprises:
    a current amplitude setting device which generates a current amplitude signal; and
    a time setting device which generates a timing signal.

5. The constant current annealing device of claim 4, wherein said current amplitdue setting device includes an amplitude thumb-wheel switch and said time setting device includes a time thumb-wheel switch.

6. The constant current annealing device of claim 1, wherein said reference circuit includes a timing programmable logic controller and a solid state relay connected to said timing programmable logic controller, said timing programmable logic controller controlling said solid state relay to generate a timing signal.

7. The constant current annealing device of claim 6, further comprising a system programmable logic controller which triggers said timing programmable logic controller to generate said timing signal when said pair of electrodes are clamped on said needle.

8. The constant current annealing device of claim 1 further comprising a current measuring device connected to one of said pair of electrodes to measure an amplitude of said constant current.

9. The constant current annealing device of claim 8, wherein said current measuring device is a hall effect transformer placed around a line connected to one of said electrodes, said constant current passing through said line.

10. The constant current annealing device of claim 8 further comprising a display connected to said current measuring device, said display displaying an indication of said amplitude of said constant current.

11. The constant current annealing device of claim 8, further comprising a system programmable logic controller which shuts off said constant current source after said amplitude deviates by a predetermined amount.

12. A constant current annealing device for annealing a surgical needle, said device comprising:
    at least one reference circuit for setting a desired annealing time and current;
    a pair of electrodes spaced apart and clamped on said needle;
    a constant current source connected to said reference circuit, said constant current source providing a constant current for annealing said needle; and
    a switching device connected between said constant current source and said pair of electrodes, said switching device switching in response to a timing signal from said reference circuit, said switching device having one position in which said constant current source provides a constant current through said pair of electrodes, and said switching device having another position in which said switching device shunts a residual current away from said pair of electrodes.

13. A constant current annealing device for annealing a surgical needle, said device comprising:
    at least one reference circuit for setting a desired annealing time and current;
    a pair of electrodes spaced apart and clamped on said needle;
    a constant current source connected to said reference circuit, said constant current source providing a constant current for annealing said needle; and
    a switching device connected between said constant current source and said pair of electrodes, said switching device switching in response to a timing signal from said reference circuit, said switching device having one position in which said constant current source provides a constant current through said pair of electrodes, and said switching device having another position in which said switching device shunts a residual current away from said pair of electrodes, and wherein the voltage drop across said switching device varies in response to chances in a voltage drop across said needle so that said current remains constant.

* * * * *